United States Patent
Skorpik et al.

[19]

[11] Patent Number: 5,906,943
[45] Date of Patent: May 25, 1999

[54] METHOD AND APPARATUS FOR CONTROLLING GAS EVOLUTION FROM CHEMICAL REACTIONS

[75] Inventors: James R. Skorpik, Kennewick; Michael G. Dodson, Richland, both of Wash.

[73] Assignee: Battelle Memorial Institute, Richland, Wash.

[21] Appl. No.: 08/700,603

[22] Filed: Aug. 14, 1996

[51] Int. Cl.$^6$ ............... G01N 33/00; C12M 1/00; G05D 9/00
[52] U.S. Cl. ............... 436/34; 436/55; 436/807; 435/287.1; 435/289.1; 422/106; 422/119
[58] Field of Search ............... 435/283.1, 287.1, 435/286.1, 286.6, 287.5, 289.1, 291.8, 296.1, 298.2, 317.1; 422/50, 62, 67, 80, 82.11, 83, 99, 127, 106, 136, 119; 436/34, 55, 807

[56] References Cited

U.S. PATENT DOCUMENTS

| | | | |
|---|---|---|---|
| 4,391,129 | 7/1983 | Trinh et al. | 73/64.4 |
| 4,524,282 | 6/1985 | King | 250/577 |
| 4,869,233 | 9/1989 | Stulen et al. | 126/374 |
| 5,252,296 | 10/1993 | Zuckermann et al. | 422/116 |
| 5,656,239 | 8/1997 | Stegemeier et al. | 422/32 |

*Primary Examiner*—Bradley L. Sisson
*Attorney, Agent, or Firm*—Paul W. Zimmerman

[57] ABSTRACT

The present invention is directed toward monitoring a thermally driven gas evolving chemical reaction with an acoustic apparatus. Signals from the acoustic apparatus are used to control a heater to prevent a run-away condition. A digestion module in combination with a robotic arm further automate physical handling of sample material reaction vessels. The invention is especially useful for carrying out sample procedures defined in EPA Methods SW-846.

1 Claim, 8 Drawing Sheets

METHOD AND APPARATUS FOR CONTROLLING GAS EVOLUTION FROM CHEMICAL REACTIONS

This invention was made with Government support under Contract DE-AC06 76RLO 1830 awarded by the U.S. Department of Energy. The Government has certain rights in the invention.

FIELD OF THE INVENTION

The present invention relates generally to a method and apparatus for controlling the rate of gas evolution from chemical reactions. More specifically, the invention relates to controlling the rate of gas evolution as bubbles through a liquid. The invention utilizes an acoustic transducer to detect the bubbles in the liquid.

BACKGROUND OF THE INVENTION

The problem of gas bubble detection in a liquid occurs in many processes from fermentation to cavitation. Bubble detection in a liquid is especially necessary in resonant chemical reactions or chemical reactions that are not self limiting. An example of a resonant chemical reaction is the reaction of highly concentrated hydrogen peroxide with organic material as temperature is increased or held constant at an elevated temperature. The hydrogen peroxide reacts with the organic material at a resonant or ever increasing rate. To avoid over pressure, overflow or other operational problems, the bubble formation must be monitored and the hydrogen peroxide/organic mixture removed from the elevated temperature environment upon observing excessive bubble formation.

More specifically, the Environmental Protection Agency (EPA) soil testing procedure EPA Method #3050 from SW-846 involves multiple acid digestion steps followed by an organic removal step utilizing highly concentrated hydrogen peroxide. In practice, multiple flasks each having a soil sample are subjected to the acid digestion and organic removal. The organic removal involves the use of concentrated (about 30 mol %) hydrogen peroxide that is heated. One of the major requirements of the EPA procedures is to avoid runaway of oxygen effervescence during organic removal. Upon observation of a run away condition, the operator immediately removes the heat source either by switching it off or by removing the flask from the heat source until the run away condition is overcome. Personnel monitoring many flasks are constantly removing run-away flasks and replacing calmed flasks in order to satisfy the EPA Methods and provide reliable soil sample preparation. Clearly, this is labor intensive and subject to human error, especially upon fatigue of the monitoring personnel.

SUMMARY OF THE INVENTION

It is an object of the present invention to provide a monitor for gas bubble evolution from a chemical reaction.

It is a further object of the present invention to provide an apparatus for handling a plurality of reaction vessels.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
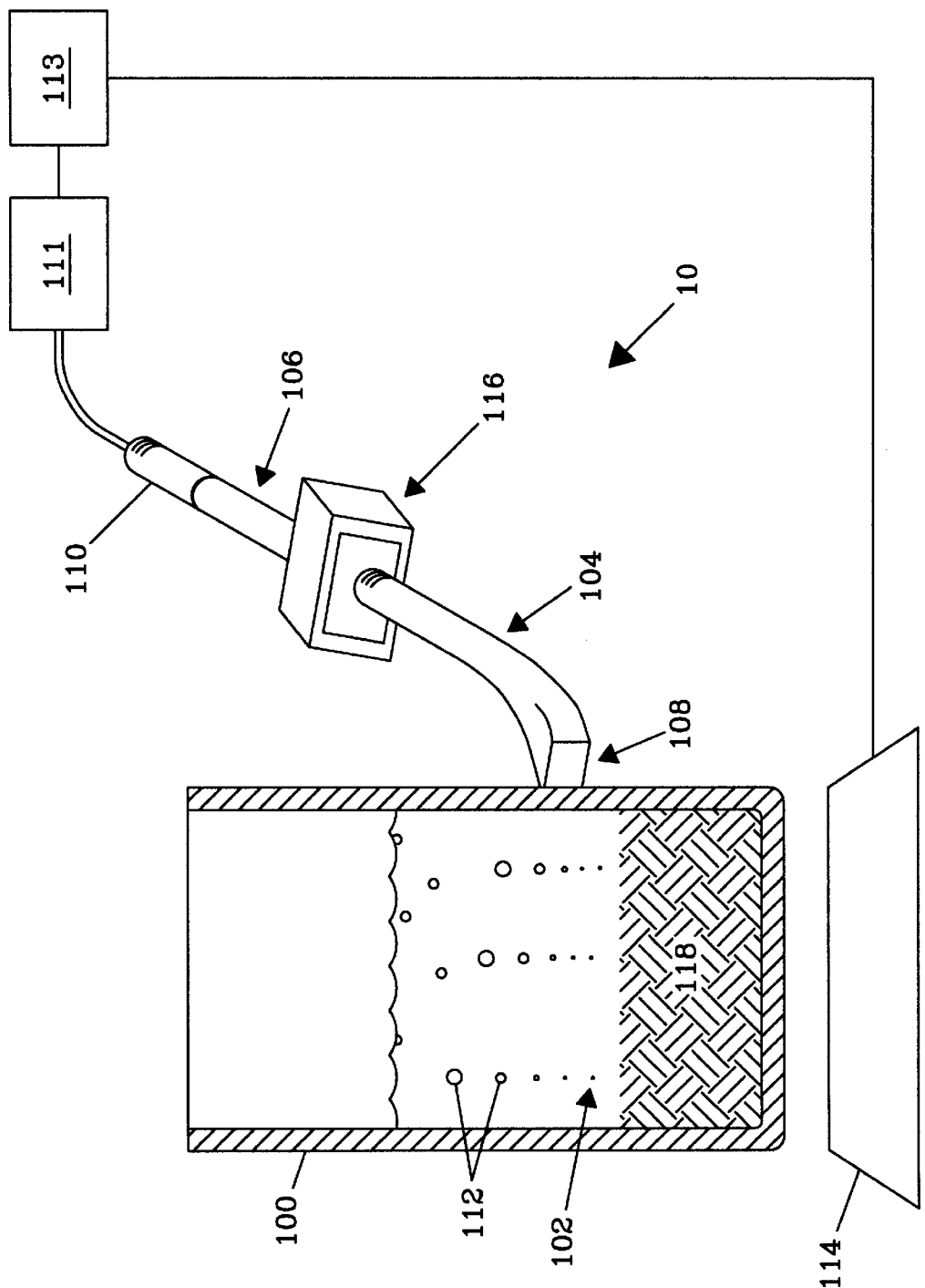
FIG. 1 is a schematic of the present invention.

The acoustic apparatus 10 of the present invention shown in FIG. 1 is for monitoring and controlling gas bubble evolution from a thermally driven chemical reaction occurring in a reaction vessel 100 containing a liquid 102. The acoustic apparatus 10 has (a) a waveguide 104 having a first end 106 and a second end 108, wherein the waveguide 104 is made of a material acoustically similar to a material of the reaction vessel 100, (b) an acoustic transducer 110 mounted on the first end 106, and (c) the second end 108 shaped to form a continuous contact with the reaction vessel 100 wherein the gas bubbles 112 form and collapse thereby providing an acoustic pressure signal through the liquid 102 into the reaction vessel 100 and thence to the second end 108, through the waveguide 104 and to the acoustic transducer 110. When the chemical reaction is thermally driven, the reaction rate may be controlled by the amount of heat provided. Accordingly, a heater 114 is provided wherein the fuel or electrical power to the heater 114 is controlled based upon signals from the acoustic transducer 110. Signal conditioning electronics 111 and a computer 113 are preferably used for heater 114 control.

Acoustically similar refers to substantially matching acoustic impedance of the waveguide 104 to the acoustic impedance of the reaction vessel 100 thereby providing maximum acoustic energy transfer. In a preferred embodiment, the reaction vessel 100 and the waveguide 104 are both made of glass.

Contact between the waveguide 104 and the reaction vessel 100 is critical. Traditionally, a couplant gel is used. However, because of the elevated temperatures of the reaction vessel 100, no couplant was used. Instead, the second end 108 of the waveguide 104 is shaped, preferably by beveling, to provide a contact to the reaction vessel 100 at an increased contact pressure. Contact is maintained preferably by a spring in the mounting bracket 116. In a preferred embodiment, the reaction vessel 100 is cylindrical and the contact is a line contact parallel to the longitudinal axis of the reaction vessel 100. The beveled shape on the second end 108 in combination with the spring loaded mounting bracket 116 further permits the waveguide 104 to be pushed out of the way when a beaker is emplaced. The waveguide 104 is preferably curved to place the first end 106 into a thermally isolated chamber or region thereby protecting the acoustic transducer 110 from the elevated digestion temperatures. For use with the acoustic emission uD30 sensors (Physical Acoustics, Princeton, N.J.) soil sample preparation apparatus, it is preferred that the angle of the curve is about 90°.

The acoustic apparatus 10 is most useful for a run-away chemical reaction, for example organic removal from a material sample 118, and more specifically, organic removal with hydrogen peroxide.

Figure 2:
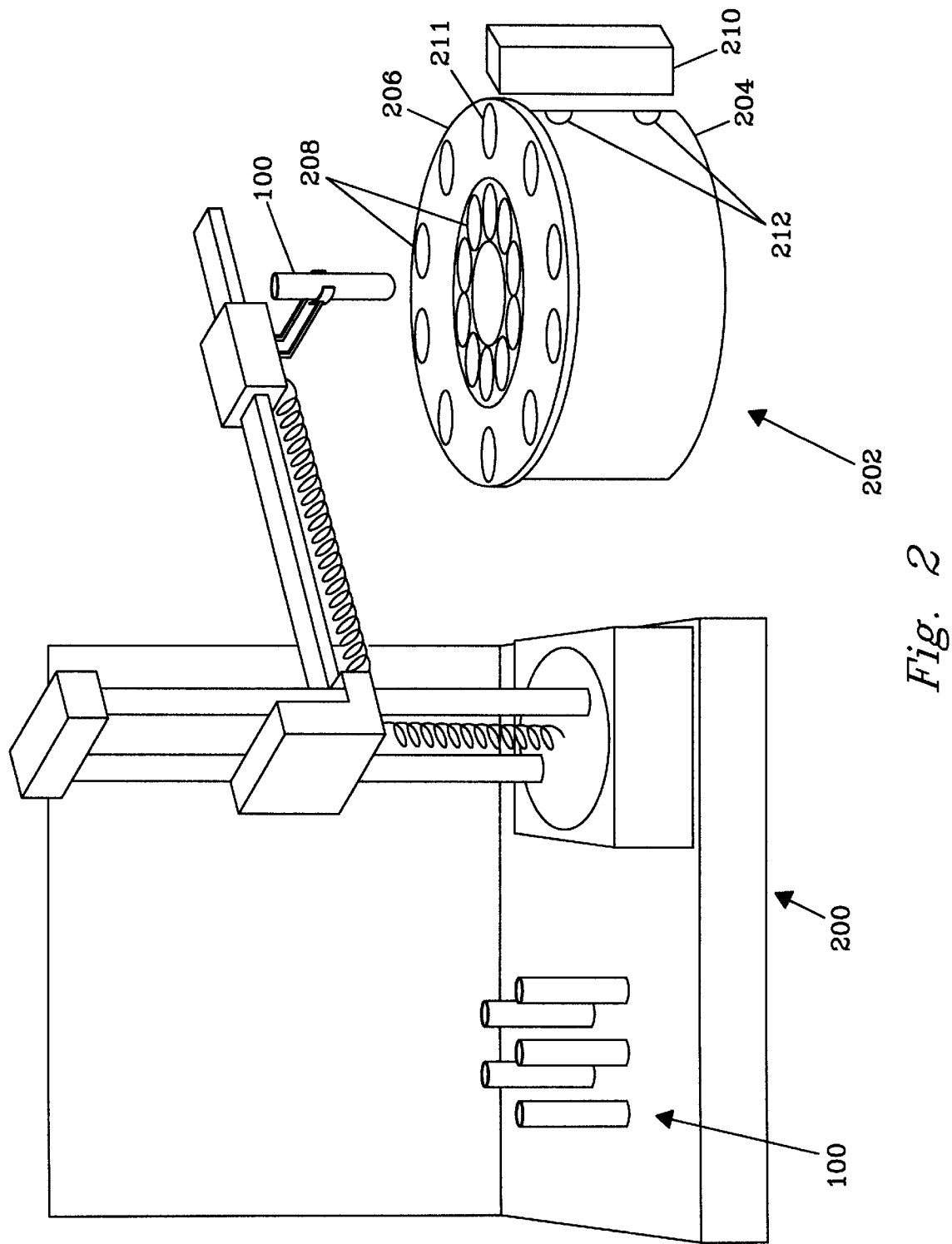
FIG. 2 is an isometric view of a sample preparation apparatus.

The acoustic apparatus 10 is especially useful in cooperation with a sample preparation instrument FIG. 2, specifically soil sample preparation for soil analysis. The soil analysis procedures are specified in EPA Methods SW-846. More specifically, EPA Method #3050 may be enhanced with the present invention: Method #3050 (SW-846 Third Edition, 9/86) ACID DIGESTION OF SEDIMENTS, SLUDGES AND SOILS.

The sample preparation instrument, in combination with the acoustic apparatus 10 is capable of performing multiple EPA Methods from SW-846 without the intervention of a human operator. One of the major requirements of the EPA procedures is to avoid runaway of oxygen effervescence during organic removal using concentrated hydrogen peroxide. The reaction rate of hydrogen peroxide with organic materials is a strong function of temperature. Even with a constant temperature, the reaction rate accelerates necessitating reduction or removal of heat to regain control of the reaction rate. It is for this reason that the reaction vessel 100 becomes heated that a waveguide 104 is necessary to avoid exposing the acoustic transducer 110 to temperatures beyond the operating parameters of the acoustic transducer.

Figure 2A:
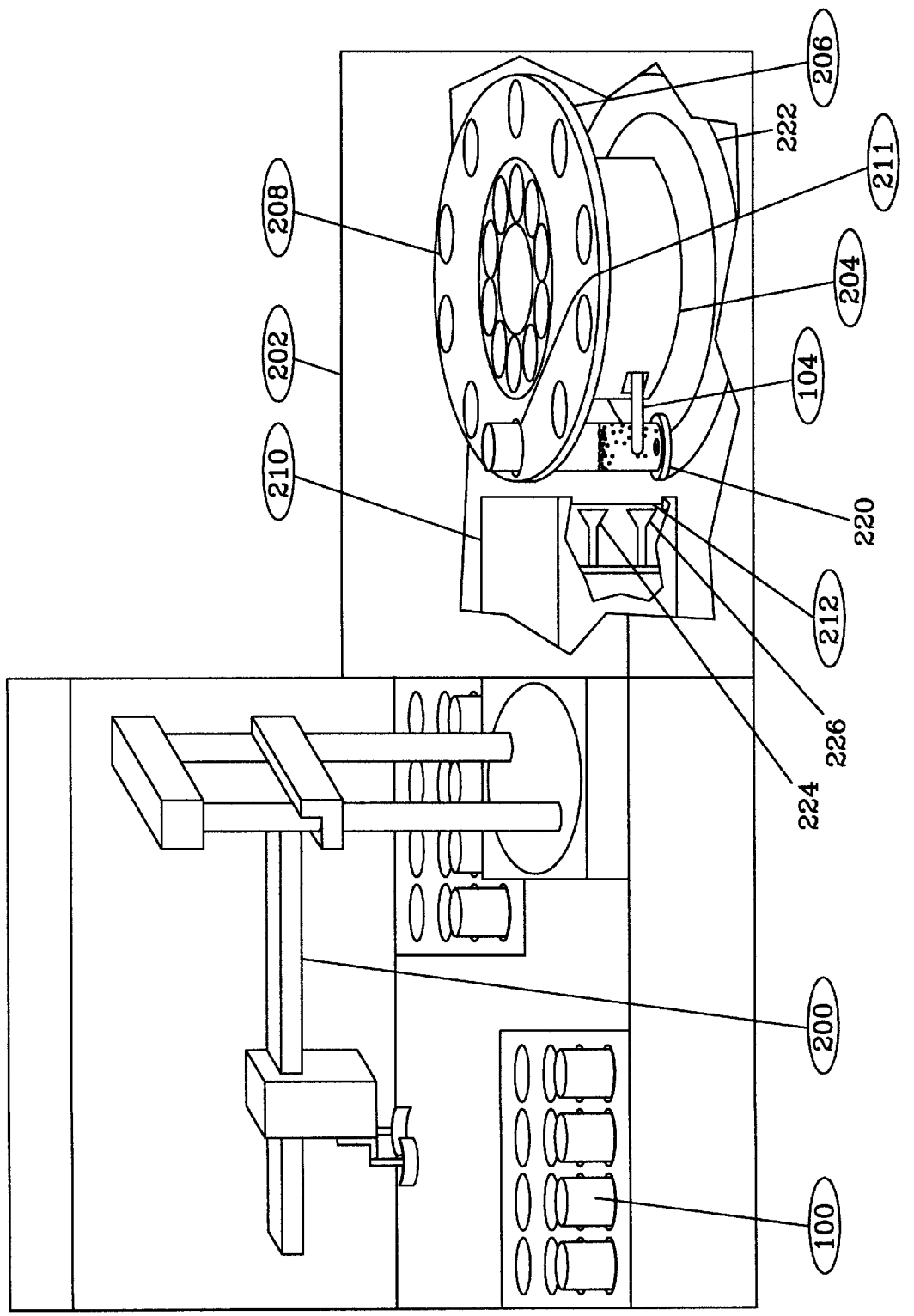
FIG. 2a is a cut-away view of a sample preparation apparatus.

Accordingly, another aspect of the present invention includes the sample preparation instrument shown in FIG. 2 for preparing a soil sample for a soil analysis. The sample preparation instrument has a robotic arm 200 for placing and removing chemical reaction vessels 100 into and from a digestion module 202. The robotic arm 200 is preferably a BenchMate manufactured by Zymark Corporation (Hopkinton, Mass.). The digestion module 202 has an outer housing 204 with a perforated cover 206. The holes 208 in the perforated cover 206 receive the reaction vessels 100. The heater 114 and the acoustic apparatus 10 are contained within the outer housing 204. The number of acoustic apparati 10 corresponds to the number of holes 208 so that each reaction vessel 100 is monitored for bubble formation. While possible to have an individual heater 114 for each reaction vessel 100, it is preferred to use a common heater 114 for all reaction vessels 100. Accordingly, upon a single reaction vessel 100 over bubbling, the heater is turned off and all reaction vessels 100 in the digestion module 202 are cooled. With this apparatus, an operator is not required to manually remove and replace reaction vessels 100 from and to the heater 114. A vision station 210 enables reaction vessel 100 presence detection, liquid level detection, and solution color detection. The housing 204 may have one or more ports 212 permitting camera view of the reaction vessel 100 in Further details are shown in FIG. 2a. A preferred embodiment of the digester 202 includes one or more reaction vessel supports 220. A heating element 222 heats the reaction vessel support(s) 220 and the reaction vessel(s) 100 by radiation and convection. The heating element 222 is preferably a Nichrome heating element. Whether circular, as shown, or serpentine, or other shape is not critical to the present invention. A circular shape is preferred for simplified construction of the digester 202. Alternatively, the reaction vessel support 220 may contain or itself be a heating element 114. The vision station 210 contains upper and lower cameras 224, 226.

The link from acoustic apparatus 10 to electronics 111 is passed through a slip-ring as is the system power. A slip-ring is required because the acoustic apparati 10 and associated electronics 111 are all mounted on the digestion module 202 that revolves.

Figure 3:
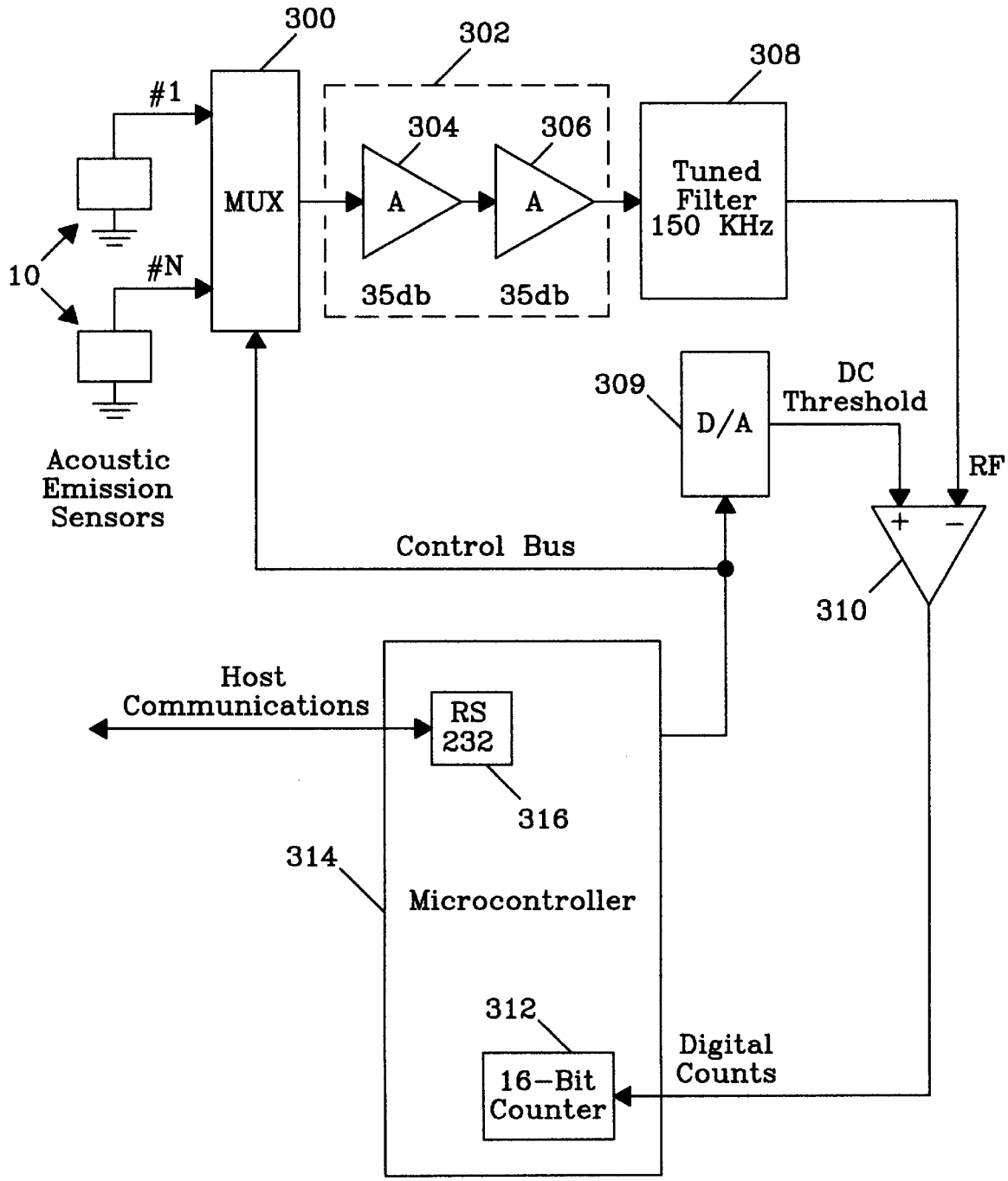
FIG. 3 is an electronic block diagram.

The data acquisition from each acoustic transducer 110 is illustrated in FIG. 3 as an electronic block diagram. The output of each acoustic apparatus 10 is continuously received into an analog multiplexer 300 which is controlled to select as its output any single one of the plurality (10) of acoustic apparatus 10 output. The analog output of the multiplexer 300 is next coupled into an amplifier 302. The level of amplification may be any amount but is typically from about 60 db to about 90 db. Preferably the amplifier is two stages of identical low noise preamps 304, 306 each having a gain of about 35 db for a total of about 70 db. Following the amplification is a frequency tuned low Q active filter 308 having a frequency matched to a selected frequency from the acoustic transducer. Preferably the frequency of the active filter is about 150 kHz. Lower frequencies are avoided so that mechanical noise of vibration from normal laboratory activities are excluded. The signal out of the active filter is finally detected by establishing a reference/detection DC threshold (provided with an digital to analog converter 309) that the active filter stage signal must exceed. This is accomplished using an analog comparator 310. Threshold set through the D/A converter 309 permits user specification of the threshold. To further quantify the detected signal, its energy is measured by counting the number of signal cycles that exceed the detection threshold with a counter 312. The multiplexer channel selection, the detection threshold setting and event counting are all performed by a single chip microcontroller 314. The microcontroller is preferably a 87C196KC made by Intel (Santa Clara, Calif.). Data is acquired by monitoring each acoustic apparatus 10 for a preset amount of time (several seconds), recording the total counts above the detection threshold and then proceeding to the next sensor. This process continues in a loop with the host computer (not shown) periodically interrupting for a status report.

The microcontroller 314 communicates to the host computer (not shown) via a serial RS-232 link 316. The microcontroller 314 receives both commands and setup information from the host computer and reports back status and data.

Because acoustic activity (bubbles 112) in a reaction vessel 100 below a certain limit indicate completion or near completion of a reaction in the reaction vessel 100 and consequently will require no modification of rate of heating, the multiplexed monitoring process for remaining reaction vessels 100 may be made faster by skipping reaction vessel (s) 100 having reduced acoustic activity. The total counts over the sampled time period (equivalent to a count rate value) are compared to an bubble activity limit. As soon as a channel has a count level below the bubble activity limit, it becomes a quiet channel and is no longer monitored and becomes tagged for reporting to the host computer. This skipping of quiet channels speeds up the multiplexed monitoring process. The bubble activity limit is user settable from the host computer.

Figure 4:
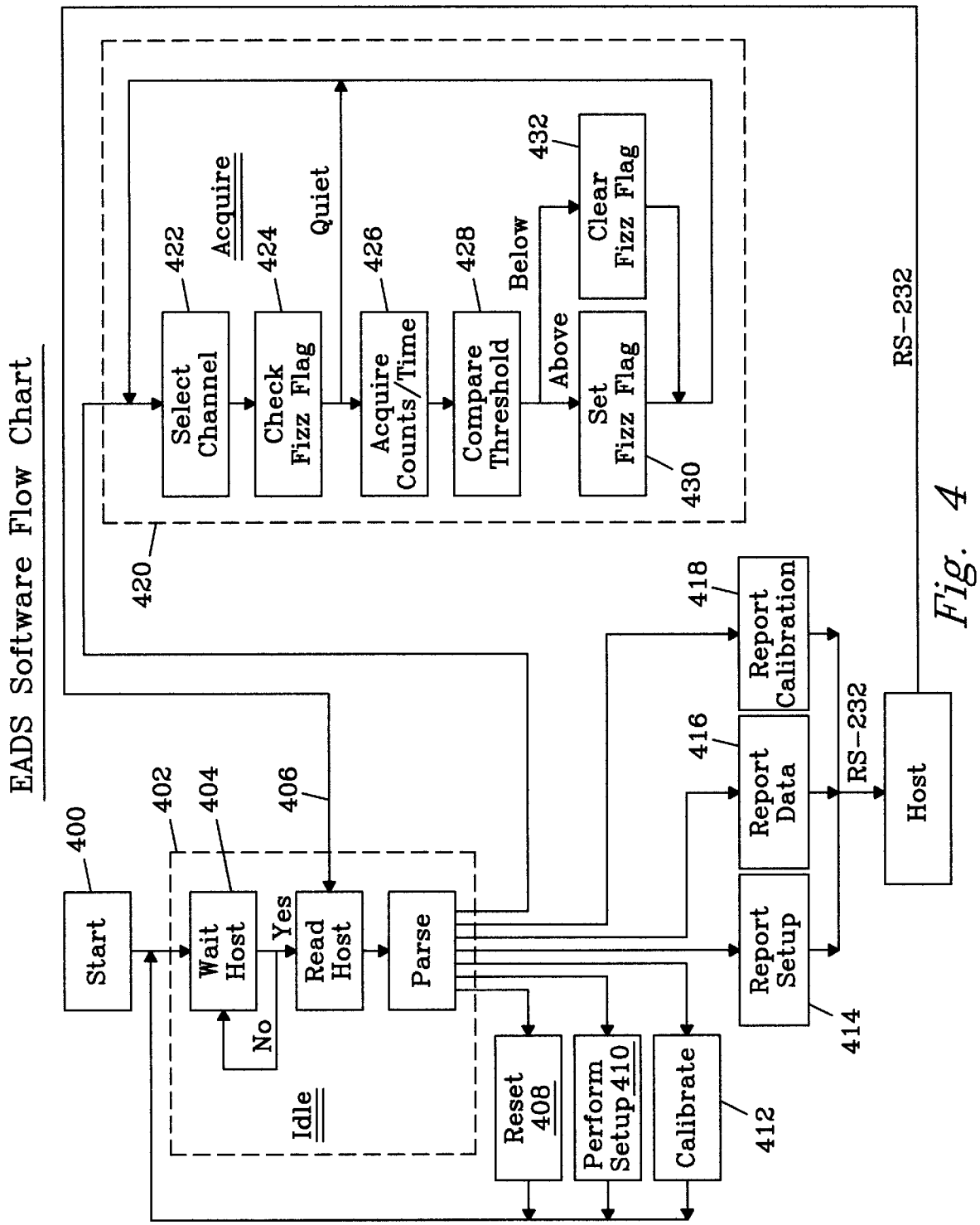
FIG. 4 is a software flow chart for bubble detection.

Software consists of assembly language code that resides in the microcontroller's internal EPROM. The software has three principle objects (1) data acquisition, (2) data analysis, and (3) host communication. FIG. 4 is a high level flowchart of these objects. The software was developed using on a desktop PC using Intel tools and the resulting executable code programmed into the chip via a hardware PROM programming unit. The third object of host communication is accomplished with a standard RS-232 serial link.

Upon power-up the microcontroller 314 containing the software depicted in FIG. 4 performs an "initialization/start" routine 400 which sets output ports that controls the electronic hardware and configures its onboard memory. The microcontroller 314 then enters an "idle mode" 402 which has a "wait host" routine 404 that scans the incoming host serial RS-232 SIO/COM port 406. Upon detecting a host send, the microcontroller 314 reads the host message string until an EOT (end-of-transmission) code is detected. The message string is next parsed separating command from setup information. The command byte is compared to the list of possible actions (1) reset 408, (2) perform setup 410, (3) calibrate 412, (4) report setup 414, (5) report data 416, (6) report calibration 418, and (7) acquire data 420. If a match is found the controller executes that particular function and then returns to the "idle mode 402 waiting for the next host action. The host has the power to preempt the microcontroller 314 at any time and terminate a function by requesting a "reset" 408 to be performed or have the microcontroller 314 execute another function such as "report data" 416.

In a preferred embodiment, the only command that utilizes supporting host information is the "perform setup" 410 which requires the host to send accompanying data that is user settable such as the reference/detection threshold. It is further preferred that the setup data is not archived in any nonvolatile memory and must be reissued upon each power-up cycle.

The software object of main interest is the "acquire module" 420 which performs the bubble detection and classification. The first step is to select a single acoustic channel 422 by outputting the proper control signals to the analog multiplexer chip 300. A "fizzing" software flag is next checked 424 to determine if this channel is quiet or active (initially all flags are set to a fizzing state and eventually cleared as the fizzing subsides). When a flag is set the channel is monitored for a preset time and the total counts logged into a corresponding memory location as a count/rate value in the acquire counts/time step 426. The value is compared to a software threshold 428 and the "fizz flag" set 430 or cleared 432 appropriately. The process returns back to the top of the acquire loop 420 and the next acoustic channel is interrogated. As each channel "fizz flag" becomes cleared that channel is no longer monitored speeding up the overall acquire cycle 420. Throughout this acquisition loop 420 the host will be asking for fizz data via the report data command 416.

Each acoustic apparatus 10 has its own calibration profile which resides in permanent storage on the host computer and is downloaded to the microcontroller 314. Individual calibration is required due to variations in each acoustic apparatus' sensitivity plus the variability in the mechanical coupling. Calibration consists of placing an calibration acoustic transducer which resides on a pedestal attached to the bottom of a calibration vessel which is filled with water. The calibration vessel is positioned so that the calibration acoustic transducer is excited with a repetitive digital pulse train and monitored with the appropriate waveguide mounted acoustic transducer 110. The detection threshold for the waveguide mounted acoustic transducer 110 is adjusted until counts are observed from the signal from the calibration acoustic transducer. Counts are collected over a set time period. This same procedure is repeated for all waveguide mounted acoustic transducers 110 and is automatically handled through interactive software on the microcontroller 314. The resulting counts provide a ratio which is logged into the host computer's permanent storage. This ratio is used to adjust the acoustic detection level when performing an automated chemical reaction, for example when doing the automated EPA procedure.

The EPA Method #3050 from SW-846 requires that 3–5 ml of liquid remain in the reaction vessel 100 after the concentration step. Reaction vessels 100 typically used in these methods are about 2 inches in diameter. Accordingly, 3–5 ml of liquid is only about 2 mm high and is difficult to measure with the naked eye. Accordingly, a miniature camera is used to image the reaction vessel 100 and the liquid 102 inside. In a preferred embodiment, the reaction vessel 100 is glass, and the miniature cameras 224, 226 are an optical miniature camera, for example a V1206 manufactured by Marshall Electronics (Culver City, Calif.). The cameras 224, 226 are also referred to as a charge coupled device (CCD). The field of view of the camera encompasses a "region of interest" (ROI).

The detection level is user settable from an external host computer. In operation (FIG. 5), a reaction vessel 100 is placed in position 211 and presented to a vision station 210 (FIG. 2) for examination. The lower camera 226 takes a vision frame and places it 500 in a frame grabber (Cortex-1 by Image Nation, Beaverton, Oreg.) consisting of a high speed A/D and digital memory along with a frame grabber microcontroller. The frame grabber microcontroller vertically scans a center portion of the frame for pixel intensity 502. The individual horizontal rows are averaged for intensity 504. This averaging smooths the vertical scan image and prevents droplets in any one area from skewing the final data. In the same manner the horizontal rows are now examined from the bottom up to find the bottom of the reaction vessel 100 which is characterized by discernable light to dark transitions 506. The image is further scanned down from the top to find another light/dark transition for the liquid meniscus 508. When the meniscus transition is identified, the positions for reaction vessel 100 bottom and meniscus height are applied to a reference data set and a curve fit made with curve fitting equations 510. The data is passed to the instrument embedded microcontroller 314 for processing to determine actual liquid height 512. The frame grabber micocontroller then makes the decision to either continue the concentration process or remove the beaker to a cooling position thus suspending the concentration process for that sample.

Figure 5:
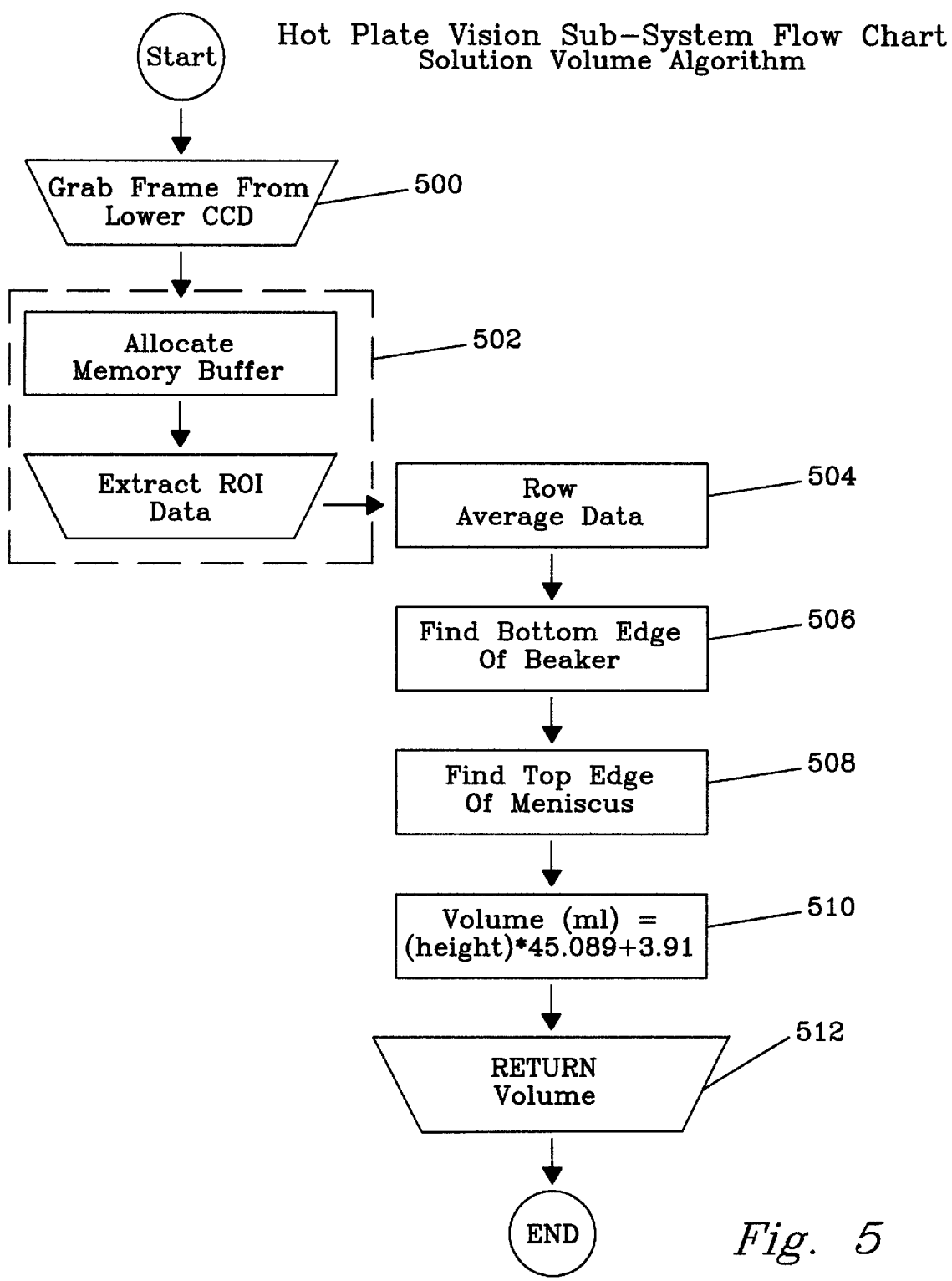
FIG. 5 is a software flow chart for solution volume or liquid height determination.
Figure 6:
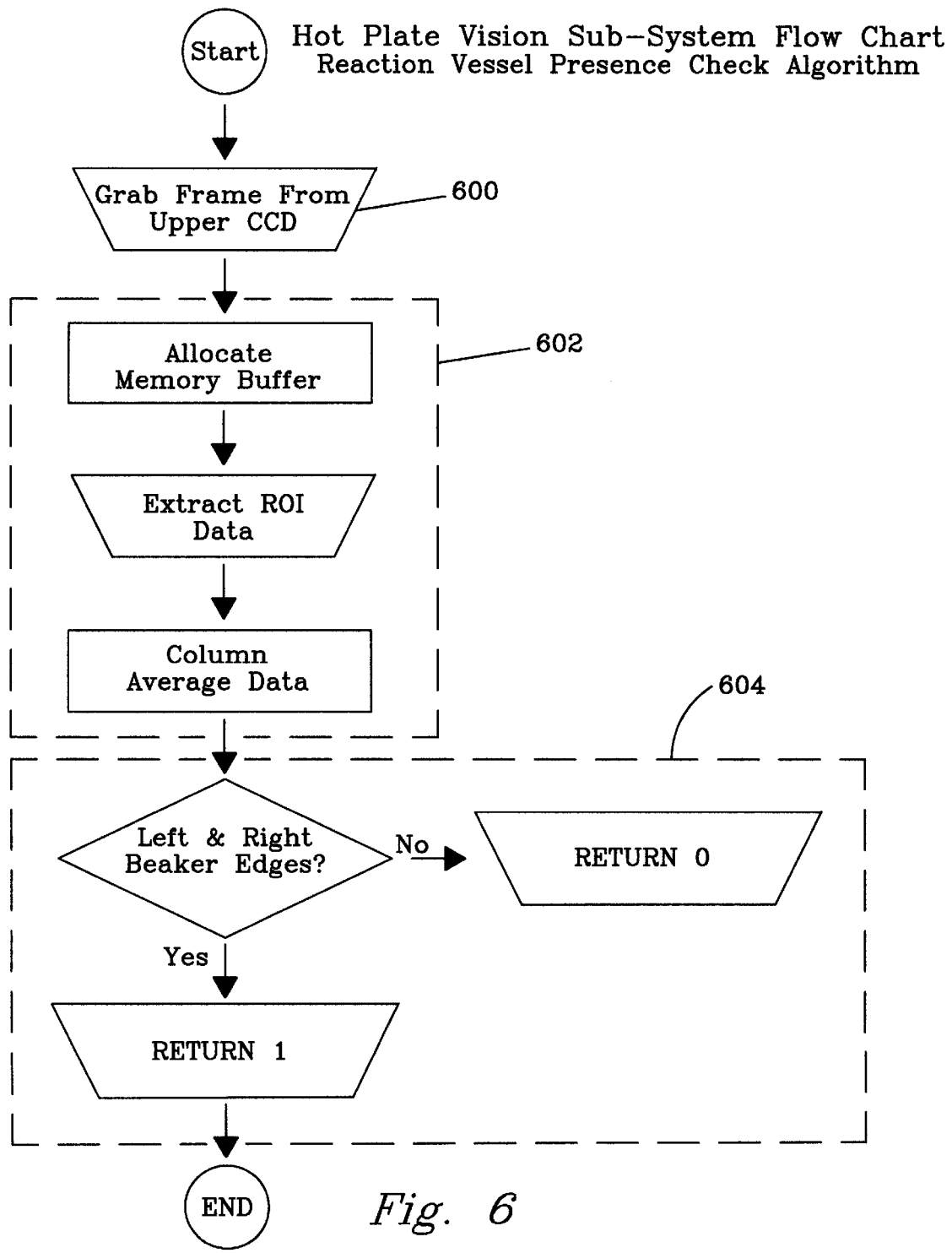
FIG. 6 is a software flow chart for reaction vessel detection.
Figure 7:
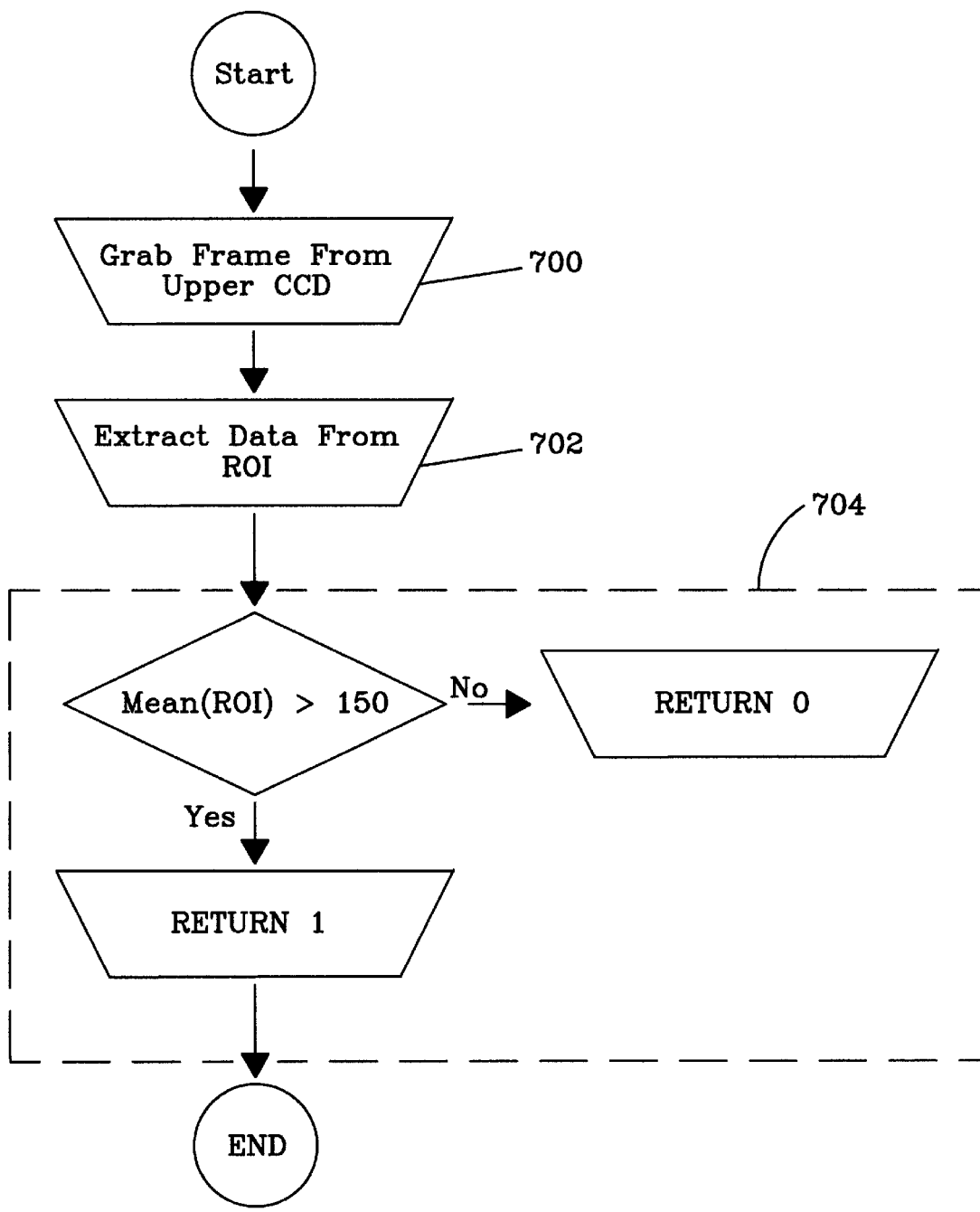
FIG. 7 is a software flow chart for solution color intensity.

As previously mentioned, the vision station 210 has upper and lower cameras. The cameras are video cameras that are used in combination with vision algorithms (FIGS. 5, 6, 7). Information from the cameras is provided to the microcontroller 314, from the frame grabber, which makes decisions about the next appropriate operation to be done. In addition to level detection, the vision station 210 has two additional tasks. 1) Reaction vessel 100 presence detection (FIG. 6): a reaction vessel 100 in one of the holes 208 is brought into position 211 and presented to the vision station 210 for examination. The upper camera 224 takes a vision frame and places it in the frame grabber for analysis 600. The image is scanned for sharp transitions from light to dark and back to light on each side of the image 602. Presence of such transitions on both sides indicates a reaction vessel 100 is in the frame. Lack of sharp transitions indicates that a reaction vessel 100 is not present. The present (value of 1), not-present (value of 0) information is passed to the microcontroller 314 for processing 604. 2) Solution color intensity (FIG. 7): A reaction vessel 100 in the position 211 is presented to the vision station 210 for examination. The lower camera 226 takes a vision frame and places it in the frame grabber for analysis 700. A central portion of the frame is extracted and pixels are averaged for image intensity 702. The average image intensity is compared to a threshold 704. This same process is repeated at a later stage in the digestion process, and the image intensities compared. Comparison results are passed to the microcontroller 314 for processing. The decision is made as to the allowable color variance per the method under examination. This is accomplished by measuring the percent change in pixel intensity.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

What is claimed is:

1. A method of preparing a plurality of soil samples for analysis, the method having at least one initial step of an acid digestion of the soil samples followed by the step of removing organic material from the soil samples wherein the removing of the organic material from the soil samples is by placing the plurality of soil samples together with hydrogen peroxide as a plurality of mixtures into a plurality of glass reaction vessels and heating the plurality of mixtures in the plurality of glass reaction vessels, monitoring a thermally driven chemical reaction of the hydrogen peroxide with the organic material within the soil samples and separating the reaction vessel from the heating upon a runaway reaction in any of the plurality of reaction vessels, wherein the improvement comprises:

(a) handling the plurality of glass reaction vessels with
  (i) a housing with a bottom and a top and sides connected thereto, the top having a perforated cover thereby receiving the plurality of glass reaction vessels, the bottom having a heater for heating the mixture; and
  (ii) placing and removing the plurality of glass reaction vessels with respect to said perforated cover with a robotic arm;

(b) wherein said monitoring is by obtaining an acoustic signal by
  (i) placing a plurality of waveguides, each having a first end and a second end, said each waveguide made of a material acoustically similar to a material of said plurality of glass reaction vessels in contact with said plurality of glass reaction vessels;
  (ii) mounting an acoustic transducer on said first end; and
  (iii) shaping said second end wherein said contact is a line contact with each of said plurality of glass reaction vessels wherein a plurality of gas bubbles form and collapse during said thermally driven chemical reaction of the hydrogen peroxide with the organic material within the soil sample thereby providing an acoustic pressure signal through the liquid into the glass reaction vessel and thence to the second end, through the waveguide and to the acoustic transducer, whereupon indication of the runaway reaction, the heating is separated from the reaction vessel; and (c) measuring a liquid depth in the glass reaction vessel with an optical level sensor having two cameras receiving light through the glass reaction vessel for providing an indication of an end of a reaction time and removal of the organic material from the soil sample based upon the liquid depth.

* * * * *